(12) United States Patent
Hunter

(10) Patent No.: US 10,166,180 B2
(45) Date of Patent: Jan. 1, 2019

(54) TREATMENT OF KERATINIZED TISSUES

(71) Applicant: Marty Richard Hunter, Surrey (CA)

(72) Inventor: Marty Richard Hunter, Surrey (CA)

( * ) Notice: Subject to any disclaimer, the term of this patent is extended or adjusted under 35 U.S.C. 154(b) by 0 days.

(21) Appl. No.: 15/439,636

(22) Filed: Feb. 22, 2017

(65) Prior Publication Data
US 2017/0157033 A1  Jun. 8, 2017

Related U.S. Application Data

(62) Division of application No. 14/214,930, filed on Mar. 15, 2014, now abandoned.

(51) Int. Cl.
| | |
|---|---|
| *A61K 8/97* | (2017.01) |
| *A61Q 5/00* | (2006.01) |
| *A61K 8/36* | (2006.01) |
| *A61K 36/886* | (2006.01) |
| *A61K 31/7004* | (2006.01) |
| *A61K 33/14* | (2006.01) |
| *A61K 31/194* | (2006.01) |
| *A61K 8/365* | (2006.01) |
| *A61K 8/49* | (2006.01) |
| *A61Q 19/00* | (2006.01) |
| *A61K 31/164* | (2006.01) |
| *A61K 8/24* | (2006.01) |
| *A61K 8/19* | (2006.01) |
| *A61K 8/20* | (2006.01) |
| *A61K 8/46* | (2006.01) |
| *A61K 8/60* | (2006.01) |
| *A61K 8/67* | (2006.01) |
| *A61K 8/86* | (2006.01) |

(52) U.S. Cl.
CPC .................. *A61K 8/97* (2013.01); *A61K 8/19* (2013.01); *A61K 8/20* (2013.01); *A61K 8/24* (2013.01); *A61K 8/36* (2013.01); *A61K 8/365* (2013.01); *A61K 8/463* (2013.01); *A61K 8/4953* (2013.01); *A61K 8/60* (2013.01); *A61K 8/673* (2013.01); *A61K 8/86* (2013.01); *A61K 31/164* (2013.01); *A61K 31/194* (2013.01); *A61K 31/7004* (2013.01); *A61K 33/14* (2013.01); *A61K 36/886* (2013.01); *A61Q 5/006* (2013.01); *A61Q 19/00* (2013.01); *A61K 2800/22* (2013.01); *A61K 2800/884* (2013.01)

(58) Field of Classification Search
CPC ... A61K 8/97; A61K 8/19; A61K 8/20; A61K 8/36; A61K 8/463; A61K 8/60; A61K 8/673; A61K 8/86; A61K 2800/22; A61K 2800/884; A61Q 5/006; A61Q 19/00
See application file for complete search history.

(56) References Cited

U.S. PATENT DOCUMENTS

2012/0076738 A1* 3/2012 Graeber ............... A61K 9/0014
424/43

FOREIGN PATENT DOCUMENTS

WO   WO 00/27356   *  5/2000

* cited by examiner

*Primary Examiner* — Blessing M Fubara
(74) *Attorney, Agent, or Firm* — Benesch Friedlander Coplan & Aronoff LLP

(57) ABSTRACT

Described are methods for treating a keratinized tissue condition in a subject in need thereof. The method may include providing the subject including the keratinized tissue condition. The method may include conducting one or more treatment cycles on the keratinized tissue. Each treatment cycle may include contacting the keratinized tissue with an acid-activated gas-generating composition. Each treatment cycle may include contacting the keratinized tissue with an acid composition. Each treatment cycle may include allowing the acid composition and the acid-activated gas-generating composition to react effective to generate a gas at the keratinized tissue. The one or more treatment cycles may be effective to at least partly ameliorate the keratinized tissue condition in the subject.

16 Claims, 1 Drawing Sheet

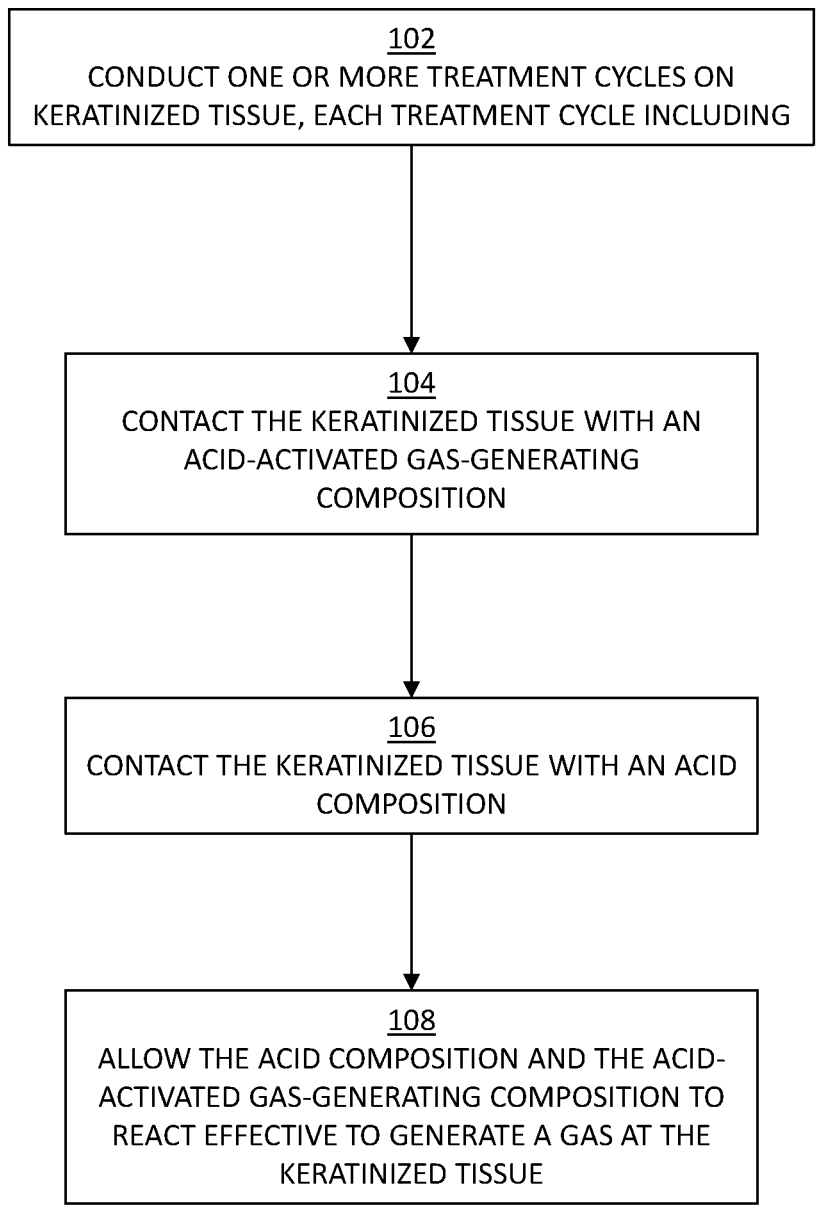

TREATMENT OF KERATINIZED TISSUES

CROSS-REFERENCE TO RELATED APPLICATIONS

This application claims priority to and is a divisional of U.S. Non-Provisional patent application Ser. No. 14/214,930, filed on Mar. 15, 2014, which is incorporated by reference herein in its entirety.

BACKGROUND

Keratinized tissues such as hair, skin, nails, fur, feathers, and the like may exhibit a variety of conditions which may have cosmetic or health implications. For example, hair may become dull, stiff, oily, easily tangled, easily frayed and the like as a result of environmental factors, endogenous health conditions, or other factors. Likewise, keratin on the surface of skin may become irritated, scaly, rough, and the like, again as a result of environmental factors, endogenous health conditions, or other factors. Areas of high skin/hair interface, such as at the scalp, may present additional issues, such as dandruff. Similar issues may affect skin, claws, fur, and feathers of nonhuman animals. Although many treatments exist to treat various conditions of keratinized tissues such treatments may suffer from issues of cost, lack of efficacy, lack of efficacy for multiple related conditions across both skin and hair, requirement for a prescription, harsh, irritating, or dangerous chemicals, and the like.

The present disclosure appreciates that ameliorating various conditions of keratinized tissues may be a challenging endeavor.

SUMMARY

In various embodiments, a method is provided for treating a keratinized tissue condition in a subject in need thereof. The method may include providing the subject including the keratinized tissue condition. The method may include conducting one or more treatment cycles on the keratinized tissue. Each treatment cycle may include contacting the keratinized tissue with an acid-activated gas-generating composition. Each treatment cycle may include contacting the keratinized tissue with an acid composition. Each treatment cycle may include allowing the acid composition and the acid-activated gas-generating composition to react effective to generate a gas at the keratinized tissue. The one or more treatment cycles may be effective to at least partly ameliorate the keratinized tissue condition in the subject.

In various embodiments, a kit is provided. The kit may be configured for treating a keratinized tissue condition in a subject in need thereof. The kit may include an acid-activated gas-generating composition or a precursor thereof included in a first reservoir. The kit may include an acid composition or a precursor thereof included in a second reservoir separated from the first reservoir. The kit may include instructions. The instructions may include directions to conduct one or more treatment cycles on the hair and/or skin. Each treatment cycle may include contacting the keratinized tissue with the acid-activated gas-generating composition. Each treatment cycle may include contacting the keratinized tissue with the acid composition. Each treatment cycle may include allowing the acid composition and the acid-activated gas-generating composition to react effective to generate a gas at the keratinized tissue.

BRIEF DESCRIPTION OF THE DRAWINGS

The accompanying FIGURES, which are incorporated in and constitute a part of the specification, illustrate example methods and apparatuses, and are used merely to illustrate example embodiments.

FIG. 1 depicts a flow chart of a method 100 for treating a keratinized tissue condition in a subject in need thereof.

DETAILED DESCRIPTION

In various embodiments, a method 100 is provided for treating a keratinized tissue condition in a subject in need thereof. FIG. 1 depicts a flow chart of a method 100. Method 100 may include 102 conducting one or more treatment cycles on the keratinized tissue. Each treatment cycle may include 104 contacting the keratinized tissue with an acid-activated gas-generating composition. Each treatment cycle may include 106 contacting the keratinized tissue with an acid composition. Each treatment cycle may include 108 allowing the acid composition and the acid-activated gas-generating composition to react effective to generate a gas at the keratinized tissue.

In some embodiments, the keratinized tissue condition may be at least partly ameliorated. The keratinized tissue condition may include one or more of, for example: acneiform eruptions, e.g., acne cosmetica, acne vulgaris, and the like; auto-inflammatory syndromes, e.g., Blau syndrome, chronic infantile neurologic cutaneous and articular syndrome, and the like; chronic blistering, e.g., pemphigus conditions, and the like; conditions of the skin appendages, e.g., folliculitis, keratosis pilaris atrophicans, and the like; dermatitis, e.g., atopic dermatitis, contact dermatitis, eczema, pustular dermatitis, seborrheic dermatitis, and the like; drug or agent eruptions, e.g., penicillin allergy, nut allergy, poison oak or poison ivy, and the like; infection-related, e.g., bacterium-related, mycobacterium-related, mycosis-related, parasitic infestations, stings, and bites, virus-related, lichenoid eruptions, and the like; papulosquamous hyperkeratosis, palmoplantar keratodermas, pruritis, e.g., itching or other sensation, and the like; psoriasis, resulting from physical factors, e.g., blisters, chapping, and the like; ionizing radiation-induced, e.g., radiation induced acne, radio-dermatitis, and the like. The keratinized tissue may include one or more of skin, hair, nails, scales, fur, and feathers. The subject may be a mammal, a bird, or a reptile. For example, the subject may be a human.

In several embodiments, at least one treatment cycle may include contacting the keratinized tissue with the acid-activated gas-generating composition before contacting the keratinized tissue with the acid composition. Additionally or alternatively, at least one treatment cycle may include contacting the keratinized tissue with the acid composition before contacting the keratinized tissue with the acid-activated gas-generating composition. The method may also include conducting two or more of the treatment cycles in succession on the keratinized tissue. Additionally or alternatively, at least one treatment cycle may include rinsing the keratinized tissue after allowing the acid composition and the acid-activated gas-generating composition to react effective to generate the gas at the keratinized tissue. Additionally or alternatively, at least one treatment cycle comprising contacting the keratinized tissue with the acid composition after conducting the one or more treatment cycles on the keratinized tissue.

In various embodiments, the method may include adjusting the keratinized tissue to between a pH of about 4.5 and a pH of about 6.5 after conducting the one or more treatment cycles on the keratinized tissue. The method may include adjusting the keratinized tissue to between a pH of about 4.5 and a pH of about 5.5 after conducting the one or more treatment cycles on the keratinized tissue.

In some embodiments, the acid-activated gas-generating composition may include one or more gas generating agents, including one or more of: an alkali metal carbonate, alkali earth metal carbonate, an alkali metal bicarbonate, an alkali earth metal bicarbonate, and carbonic acid. For example, alkali metals may include lithium, sodium, potassium, cesium, and the like. Alkali earth metals may include beryllium, magnesium, calcium, strontium, barium, and the like. The acid composition may include an acid including one or more of: lactic acid, acetic acid, formic acid, citric acid, oxalic acid, phosphoric acid, succinic acid, uric acid, an acidic ammonium salt such as ammonium chloride, and the like.

In several embodiments, the acid-activated gas-generating composition and the acid composition may each independently include one or more of: water; aloe vera extract; panthenol; a sugar, e.g. dextrose; an ionic surfactant, e.g., sodium lauryl sulfoacetate; a water soluble alkali metal halide salt, e.g., sodium chloride; a water soluble alkali earth metal salt, e.g., magnesium chloride; a nonionic surfactant, e.g., polyethylene oxide, a preservative, e.g., sodium benzoate; and sea trace elements. For example, the acid-activated gas-generating composition may include an acid-activated gas-generating agent such as sodium hydrogen carbonate as well as water, aloe vera extract, panthenol, dextrose, polyethylene oxide, sodium benzoate, sodium chloride, magnesium chloride, sodium lauryl sulfoacetate, dextrose, and sea trace elements. Further, for example, the acid composition may include an acid agent such as citric acid as well as water, aloe vera extract, panthenol, dextrose, polyethylene oxide, sodium benzoate, sodium chloride, magnesium chloride, and sea trace elements. The acid-activated gas-generating composition may include one or more of: a water soluble alkali metal halide salt, a water soluble alkali earth metal salt, an ionic surfactant, a sugar, and sea trace elements. The acid activated gas generating composition may include sodium hydrogen carbonate, a water soluble alkali metal halide salt, e.g., sodium chloride, a water soluble alkali earth metal salt, e.g., magnesium chloride; a sugar, e.g., dextrose; and sea trace elements. The acid composition may include citric acid, sodium chloride, magnesium chloride, dextrose, and sea trace elements. In various embodiments, the acid-activated gas-generating composition may omit the sea trace elements. The acid composition may omit the sea trace elements.

In various embodiments, the method may include contacting the keratinized tissue with the acid-activated gas-generating composition causing a pH value of the keratinized tissue to be greater than about 7. Contacting the keratinized tissue with the acid composition may cause a pH value of the keratinized tissue to be less than about 7. At least one of the one or more treatment cycles may cause the keratinized tissue to vary in pH between an alkaline state and an acidic state. One or more of the acid-activated gas-generating composition and the acid composition may include a pH indicator. The acid-activated gas-generating composition and the acid composition may collectively comprise an acidic pH indicator and an alkaline pH indicator.

In some embodiments, the keratinized tissue may include a plurality of cuticles. At least one of the one or more treatment cycles may include a pH value at the keratinized tissue effective to cause at least a portion of the plurality of cuticles to switch between an open state and a closed state. The keratinized tissue may include a plurality of keratinized epidermal skin cells. At least one of the one or more treatment cycles may cause a pH at the keratinized tissue to vary effective to cause at least a portion of the plurality of keratinized epidermal skin cells to be shed from the keratinized tissue.

In several embodiments, the method may include preparing the acid-activated gas-generating composition by contacting a precursor of the acid-activated gas-generating composition with one or more of: water and a slip composition. The method may include preparing the acid composition by contacting a precursor of the acid composition with one or more of: water and the slip composition. The slip composition may include one or more of: water, aloe vera extract, panthenol, a sugar, a nonionic surfactant, a preservative, a water soluble alkali metal halide salt, a water soluble alkali earth metal salt, an ionic surfactant, and sea trace elements.

In various embodiments, a kit is provided. The kit may be configured for treating a keratinized tissue condition in a subject in need thereof. The kit may include an acid-activated gas-generating composition or a precursor thereof included in a first reservoir. The kit may include an acid composition or a precursor thereof included in a second reservoir separated from the first reservoir. The kit may include instructions. The instructions may include directions to conduct one or more treatment cycles on the keratinized tissue, e.g., hair and/or skin. Each treatment cycle may include contacting the keratinized tissue with the acid-activated gas-generating composition. Each treatment cycle may include contacting the keratinized tissue with the acid composition. Each treatment cycle may include allowing the acid composition and the acid-activated gas-generating composition to react effective to generate a gas at the keratinized tissue.

In some embodiments, the first reservoir may include the precursor of the acid-activated gas-generating composition. The kit may also include a slip composition included in a third reservoir. The slip composition may include or more of: water, aloe vera extract, panthenol, a sugar, a nonionic surfactant, a preservative, a water soluble alkali metal halide salt, a water soluble alkali earth metal salt, an ionic surfactant, a sugar, and sea trace elements. The kit may further include instructions to combine the slip composition with the precursor of the acid-activated gas-generating composition in the first reservoir to form the acid-activated gas-generating composition. Alternatively or in addition, the kit may include instructions to combine the slip composition with the precursor of the acid composition in the second reservoir to form the acid composition.

In various embodiments, the kit may further comprise instructions to contact water to the precursor of the acid-activated gas-generating composition in the first reservoir. The kit may further include instructions to contact water to the precursor of the acid composition in the second reservoir.

In several embodiments, the instructions may include instructions for carrying out any method operation described herein. For example, the instructions may direct a user to continue treating the keratinized tissue until the keratinized tissue condition may be at least partly ameliorated.

In various embodiments, the instructions may direct a user to treat a keratinized tissue condition including one or more of: acneiform eruptions, e.g., acne cosmetica, acne vulgaris, and the like; auto-inflammatory syndromes, e.g., Blau syndrome, chronic infantile neurologic cutaneous and articular syndrome, and the like; chronic blistering, e.g., pemphigus conditions, and the like; conditions of the skin appendages, e.g., folliculitis, keratosis pilaris atrophicans, and the like; dermatitis, e.g., atopic dermatitis, contact dermatitis, eczema, pustular dermatitis, seborrheic dermatitis, and the like; drug or agent eruptions, e.g., penicillin allergy, nut allergy, poison oak or poison ivy, and the like; infection-related, e.g., bacterium-related, mycobacterium-related, mycosis-related, parasitic infestations, stings, and bites, virus-related, lichenoid eruptions, and the like; papulosquamous hyperkeratosis; palmoplantar keratodermas; pruritis, e.g., itching or other sensation, and the like; psoriasis, resulting from physical factors, e.g., blisters, chapping, and the like; ionizing radiation-induced, e.g., radiation induced acne, radio-dermatitis, and the like.

In some embodiments, the instructions may direct a user to treat a keratinized tissue including one or more of: skin, hair, nails, scales, fur, and feathers. The instructions may direct a user to treat a keratinized tissue in a subject that may be a mammal, a bird, or a reptile. For example, the subject may be a human.

In several embodiments, the instructions may direct a user to treat a keratinized tissue in at least one treatment cycle including contacting the keratinized tissue with the acid-activated gas-generating composition before contacting the keratinized tissue with the acid composition. The instructions may direct a user to treat a keratinized tissue in at least one treatment cycle including contacting the keratinized tissue with the acid composition before contacting the keratinized tissue with the acid-activated gas-generating composition. The instructions may direct a user to treat a keratinized tissue by conducting at least two or more of the treatment cycles in succession on the keratinized tissue. For example, the instructions may direct a user to conduct at least about 2, 3, 4, 5, 6, 7, 8, 9, 10, 11, 12, 13, 14, 15, 16, 17, 18, 19, 20, 21, 22, 23, 24, 25, or more treatment cycles in a treatment session. The instructions may direct a user to treat a keratinized tissue in at least about 1, 2, 3, 4, 5, 6, 7, 8, 9, 10, 11, 12, 13, 14, 15, 16, 17, 18, 19, 20, 21, 22, 23, 24, 25, or more treatment sessions of the treatment cycles described herein. The instructions may direct a user to treat a keratinized tissue by at least one treatment cycle including rinsing the keratinized tissue after allowing the acid composition and the acid-activated gas-generating composition to react effective to generate the gas at the keratinized tissue. The instructions may direct a user to treat a keratinized tissue by at least one treatment cycle including contacting the keratinized tissue with the acid composition after conducting the one or more treatment cycles on the keratinized tissue.

In various embodiments, in the kit, the acid-activated gas-generating composition may include one or more gas generating agents, including one or more of: an alkali metal carbonate, alkali earth metal carbonate, an alkali metal bicarbonate, an alkali earth metal bicarbonate, and carbonic acid. For example, alkali metals may include lithium, sodium, potassium, cesium, and the like. Alkali earth metals may include beryllium, magnesium, calcium, strontium, barium, and the like.

In some embodiments, in the kit, the acid composition may include an acid including one or more of: lactic acid, acetic acid, formic acid, citric acid, oxalic acid, phosphoric acid, succinic acid, uric acid, and an acidic ammonium salt. The acid composition may include an acid comprising one or more of: lactic acid, acetic acid, formic acid, citric acid, oxalic acid, phosphoric acid, succinic acid, uric acid, an acidic ammonium salt such as ammonium chloride, and the like.

In several embodiments, in the kit, the acid-activated gas-generating composition and the acid composition may each independently include one or more of: water; aloe vera extract; panthenol; a sugar, e.g. dextrose; an ionic surfactant, e.g., sodium lauryl sulfoacetate; a water soluble alkali metal halide salt, e.g., sodium chloride; a water soluble alkali earth metal salt, e.g., magnesium chloride; a nonionic surfactant, e.g., polyethylene oxide, a preservative, e.g., sodium benzoate; and sea trace elements. For example, the acid-activated gas-generating composition may include an acid-activated gas-generating agent such as sodium hydrogen carbonate as well as water, aloe vera extract, panthenol, dextrose, polyethylene oxide, sodium benzoate, sodium chloride, magnesium chloride, sodium lauryl sulfoacetate, dextrose, and sea trace elements. Further, for example, the acid composition may include an acid agent such as citric acid as well as water, aloe vera extract, panthenol, dextrose, polyethylene oxide, sodium benzoate, sodium chloride, magnesium chloride, and sea trace elements. In the kit, the acid activated gas generating composition may include sodium hydrogen carbonate, a water soluble alkali metal halide salt, e.g., sodium chloride, a water soluble alkali earth metal salt, e.g., magnesium chloride; a sugar, e.g., dextrose; and sea trace elements. In the kit, the acid composition may include citric acid, sodium chloride, magnesium chloride, dextrose, and sea trace elements.

In various embodiments, in the kit, one or more of the acid-activated gas-generating composition and the acid composition may include a pH indicator. For example, one or more of the acid-activated gas-generating composition and the acid composition may collectively include an acidic pH indicator and an alkaline pH indicator. The instructions may direct a user to treat a keratinized tissue by adjusting the keratinized tissue to between a pH of about 4.5 and a pH of about 6.5 after conducting the one or more treatment cycles on the keratinized tissue. The instructions may direct a user to contact the keratinized tissue with the acid-activated gas-generating composition effective to cause a pH value of the keratinized tissue to be greater than about 7. The instructions may direct a user to contact the keratinized tissue with the acid composition causing a pH value of the keratinized tissue to be less than about 7. The instructions may direct a user to conduct at least one of the one or more treatment cycles effective to cause the keratinized tissue to vary in pH between an alkaline state and an acidic state. The instructions may direct a user to conduct at least one of the one or more treatment cycles varying a pH value at the keratinized tissue effective to cause at least a portion of a plurality of cuticles of the keratinized tissue to switch between an open state and a closed state. The instructions may direct a user to conduct at least one of the one or more treatment cycles causing a pH at the keratinized tissue to vary effective to cause at least a portion of a plurality of keratinized epidermal skin cells to be shed from the keratinized tissue.

Example 1: Treatment of Dandruff

Observed Condition Prior to Treatment:

A 53 year old Caucasian female presented with a medium fine hair in a relatively thick density at the subject's scalp. Prior to treatment, the subject complained of a very tight-feeling and itchy, dry scalp. Multiple areas of flaking dry dandruff were observed on the scalp and visible dandruff was observed on the subject's clothing, mostly in the shoulder area. Visible, reddish pink irritations were observed on the scalp in multiple areas. Dandruff was observed to be scattered throughout the scalp, at areas of the reddish pink irritations and at apparently non-irritated areas. Some of the irritations appeared circular in nature with the center of the circle appearing unaffected, or less affected; while no specific diagnosis was made, this circular irritation model is consistent with various fungal infections. Other areas of solid irritations were observed to be approximately 0.5 to 1.5 cm in size. A physician commented on the preceding description and suggested the subject could have been suffering from Tinea Capitis or ringworm of the scalp, a fungal infection, and/or seborrheic eczema.

Compositions:

An acid-activated gas-generating composition was prepared in a first squirt bottle by adding 20 mL of a Slip composition and warm tap water (XX mL). The Slip composition included water, Aloe Vera Extract (*Aloe Barbensis* leaf extract), panthenol, (Pantothenic acid (Vitamin B5)), dextrose, polyethylene oxide, and sodium benzoate. The first squirt bottle also contained sodium hydrogen carbonate, sodium chloride, magnesium chloride, sodium lauryl sulfoacetate, dextrose, and sea trace elements. The combined contents of the first squirt bottle were mixed by shaking to form a uniform solution of the acid-activated gas-generating composition, which had an alkaline pH.

An acid composition was prepared in a second squirt bottle by adding 20 mL of a Slip composition and warm tap water (XX mL). The Slip composition included water, Aloe Vera Extract (*Aloe Barbensis* leaf extract), panthenol, (Pantothenic acid (Vitamin B5)), dextrose, polyethylene oxide, and sodium benzoate. The second squirt bottle also contained citric acid, sodium chloride, magnesium chloride, dextrose, and sea trace elements. The combined contents of the second squirt bottle were mixed by shaking to form a uniform solution of the acid composition, which had an acidic pH.

Treatment:

The subject's hair and scalp was first washed with a conventional hydrating shampoo according to the manufacturer's directions. Subsequently, a treatment cycle was performed by contacting the subject's hair and scalp sequentially with roughly equal volumes of the acid-activated gas-generating composition and the acid composition. Contacting the acid-activated gas-generating composition with the acid composition led to rapid gas generation and bubbling at the hair/scalp, which the subject experienced as a refreshing tingling sensation. The treatment cycle was repeated about 10 more times, ending with the acid composition to give the hair and scalp an acidic pH. The subject's hair and scalp were then rinsed well with warm water. A conventional hair conditioner was applied and rinsed according to the manufacturer's directions. The subject's hair was then dried. The preceding steps were repeated 3 more times over a two-week period totaling four treatment sessions.

Results:

After the four treatment sessions, the subject's hair and scalp was examined. No signs of dandruff or reddish irritations were observed on the subject's scalp. The subject reported that the dryness, tight scalp and itching was ameliorated over the course of the four treatment sessions.

Discussion:

Without wishing to be bound by theory, possible reasons for changes on the subject's hair and scalp are presented. Humans may display some form of dandruff throughout their lives and at many different times. Seborrheic eczema is also very common in humans. Conditions such as Tinea Capitis may be caused or exacerbated by fungus and yeast. Seborrheic Eczema may be caused, exacerbated, or associated with the overproduction of oil by the scalp. The yeast *Malassezia*, formerly *Pityrosporum*, is a fungi genus believed to be the cause of many cases of dandruff and seborrheic dermatitis. The yeast *Malassezia* is common on the human scalp because it requires lipids to grow and is observed to be concentrated near the sebaceous glands of the scalp. When a skin infection due to fungi and/or bacteria grows rapidly, it is believed that the natural renewal of skin cells may be disturbed and dandruff and itching may occur. In the case of *Malassezia*, lipases and phospholipases are employed to metabolize and break down lipids found in the oils of the scalp. *Malassezia* is a facultative anaerobe and may grow best in the presence of oxygen, but does not require oxygen. It is believed that treatment according to the present example may create a less favorable environment for the yeast, such that fewer numbers should be reproduced in a given period of time compared to untreated hair and scalp which may reduce the occurrence of dandruff. The carbon dioxide evolved may decrease local oxygen concentrations and impair yeast growth. Further, the surfactant (Sodium Lauryl Sulfoacetate) employed in the acid-activated gas-generating composition may have reduced the amount of oil on the scalp and hair, perhaps "starving" the remaining yeast of necessary nutrients for reproduction and cellular metabolism. Also, the stimulation to the scalp provided by the gas evolution may increase the blood supply and may loosen and help remove dead skin cells.

Example 2: Treatment of Hand Skin Condition

Observed condition prior to treatment: A 67 year old Caucasian male presented with a physician's diagnosis of psoriasis on many parts of his body including the palms of his hands. The subject complained that his hands are treated with painful steroid injections into the palms of his hands by his dermatologist once a week. The sites on the hands were observed with open wounds where the underlying tissue was exposed and was weeping slightly. The sites on the subject's hands were observed with a dark purple coloration and dead skin scaling off of the surface. The subject explained that the sites burn terribly and worse with the contact of hot water. The subject also reported being self-conscious of his hands to the point that he avoids shaking people's hands. The subject reported trouble sleeping at night due to the pain experienced in his hands. The subject reported application of hand lotion to try to hydrate his hands, but with aggravation of the affected areas and with an undesirable "stinging" sensation.

Compositions:

The acid-activated gas-generating composition and acid composition were prepared as described in EXAMPLE 1, except that sodium lauryl sulfoacetate was not present to avoid further drying of the subject's hands.

Treatment:

The subject's hands were treated with 10 consecutive treatment cycles, constituting a treatment session, each cycle beginning with the acid-activated gas-generating composition and ending with the acid composition to leave the skin at an acidic pH. The subject received at least three treatment sessions per week over a three month period.

Results:

The subject reported cessation of the steroid injections as a result of the treatment described above. Further, the subject's hands were observed to have educed flaking skin and the absence of open lesions; improved skin color, with reduced purple and grey coloration. The subject reported cessation of pain, itching, and burning as a result of the treatment sessions. The subject reported increased self-confidence and well-being due to the improvement to his hands. The subject reported a normal routine of bathing and hand washing.

Discussion:

Without wishing to be bound by theory, the results from the multiple treatments to the subject's hands seems to have caused both a physiological and psychological improvement to the subject. Results are physically visible. Psychological effects were also reported. The subject claims that his comfort level has never been this good since diagnosed with this affliction.

Example 3: Treatment of Dandruff

Observed Condition Prior to Treatment:

A 48 year old Caucasian female presented with severe dandruff. The subject had relatively thick hair at a relatively thick density. Moderate to severe dandruff was observed covering most of the scalp and even behind the ears. Dandruff was observed all over the scalp, with more pronounced symptoms towards the front hairline and the nape of the neck. The subject reported the dandruff had been a chronic condition all of her life. The subject reported that her scalp is often tight and dry feeling, and that her whole scalp was itchy.

Compositions:

The acid-activated gas-generating composition and acid composition were prepared as described in EXAMPLE 1.

Treatment:

The subject's hair and scalp was first washed with a conventional hydrating shampoo according to the manufacturer's directions. Subsequently, a treatment session including 10 treatment cycles was performed, each treatment cycle conducted by contacting the subject's hair and scalp sequentially with roughly equal volumes of the acid-activated gas-generating composition and the acid composition. Contacting the acid-activated gas-generating composition with the acid composition led to rapid gas generation and bubbling at the hair/scalp, which the subject experienced as a refreshing tingling sensation. Each treatment cycle caused the pH at the hair and scalp to cycle between alkaline and acid. After a period of several weeks, the subject returned and a second treatment session was conducted. Subsequently, further treatment sessions were conducted every five weeks for a period of several months.

Results:

After the first two treatment sessions, the subject's hair and scalp was examined. Compared to before the two treatment sessions, the subject's scalp was 95% free of dandruff. Very little physical appearance of dandruff was observed. The subject reported that the dryness, tight scalp and itching was ameliorated over the course of the two treatment sessions. Moreover, the subject reported that the dandruff was ameliorated after the first treatment session and was dandruff-free up to the second treatment session. The subject reported that she has never been this dandruff-free in her whole adult life, despite trying numerous shampoos and conditioners that claim to help with removing dandruff. Because the subject was in a new environment between the first and second treatment sessions, external stimuli could not be excluded as a cause of the initial dandruff amelioration after the first treatment session. However, the fact that dandruff remained ameliorated over treatment sessions subsequent to the second treatment session, when the subject had returned to her normal environment, strongly suggests that the observed dandruff amelioration was caused by the treatment sessions.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the terms "coupled" or "operatively connected" are used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 cells refers to groups having 1, 2, or 3 cells. Similarly, a group having 1-5 cells refers to groups having 1, 2, 3, 4, or 5 cells, and so forth. While various aspects and embodiments have been disclosed herein, other aspects and embodiments will be apparent to those skilled in the art.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

As used herein, "substituted" refers to an organic group as defined below (e.g., an alkyl group) in which one or more bonds to a hydrogen atom contained therein may be replaced by a bond to non-hydrogen or non-carbon atoms. Substituted groups also include groups in which one or more bonds to a carbon(s) or hydrogen(s) atom may be replaced by one or more bonds, including double or triple bonds, to a heteroatom. A substituted group may be substituted with one or more substituents, unless otherwise specified. In some embodiments, a substituted group may be substituted with 1, 2, 3, 4, 5, or 6 substituents. Examples of substituent groups include: halogens (e.g., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; or nitriles. A "per"-substituted compound or group is a compound or group having all or substantially all substitutable positions substituted with the indicated substituent. For example, 1,6-diiodo perfluoro hexane indicates a compound of formula $C_6F_{12}I_2$, where all the substitutable hydrogens have been replaced with fluorine atoms.

Substituted ring groups such as substituted cycloalkyl, aryl, heterocyclyl and heteroaryl groups also include rings and ring systems in which a bond to a hydrogen atom may be replaced with a bond to a carbon atom. Substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some examples, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above and include, without limitation, haloalkyl (e.g., trifluoromethyl), hydroxyalkyl, thioalkyl, aminoalkyl, alkylaminoalkyl, dialkylaminoalkyl, alkoxyalkyl, or carboxyalkyl.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments, the number of ring carbon atoms ranges from 3 to 5, 3 to 6, or 3 to 7. Bi- and tricyclic ring systems include both bridged cycloalkyl groups and fused rings, such as, but not limited to, bicyclo[2.1.1] hexane, adamantyl, or decalinyl. Substituted cycloalkyl groups may be substituted one or more times with non-hydrogen and non-carbon groups as defined above. However, substituted cycloalkyl groups also include rings that may be substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Aryl groups may be cyclic aromatic hydrocarbons that do not contain heteroatoms. Aryl groups herein include monocyclic, bicyclic and tricyclic ring systems. Aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups may be phenyl or naphthyl. Although the phrase "aryl groups" may include groups containing fused rings, such as fused aromatic-aliphatic ring systems (e.g., indanyl or tetrahydronaphthyl), "aryl groups" does not include aryl groups that have other groups, such as alkyl or halo groups, bonded to one of the ring members. Rather, groups such as tolyl may be referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl, which may be substituted with substituents such as those above.

Aralkyl groups may be alkyl groups as defined above in which a hydrogen or carbon bond of an alkyl group may be replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Substituted aralkyls may be substituted one or more times with substituents as listed above.

Groups described herein having two or more points of attachment (e.g., divalent, trivalent, or polyvalent) within the compound of the technology may be designated by use of the suffix, "ene." For example, divalent alkyl groups may be alkylene groups, divalent aryl groups may be arylene groups, divalent heteroaryl groups may be heteroarylene groups, and so forth. In particular, certain polymers may be described by use of the suffix "ene" in conjunction with a term describing the polymer repeat unit.

Alkoxy groups may be hydroxyl groups (—OH) in which the bond to the hydrogen atom may be replaced by a bond to a carbon atom of a substituted or unsubstituted alkyl group as defined above. Examples of linear alkoxy groups include, but are not limited to, methoxy, ethoxy, propoxy, butoxy, pentoxy, or hexoxy. Examples of branched alkoxy groups include, but are not limited to, isopropoxy, secbutoxy, tert-butoxy, isopentoxy, or isohexoxy. Examples of cycloalkoxy groups include, but are not limited to, cyclopropyloxy, cyclobutyloxy, cyclopentyloxy, or cyclohexyloxy. Representative substituted alkoxy groups may be substituted one or more times with substituents such as those listed above.

The term "amine" (or "amino"), as used herein, refers to $NR_5R_6$ groups, wherein $R_5$ and $R_6$ may be independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine may be alkylamino, dialkylamino, arylamino, or alkylarylamino. In other embodiments, the amine may be $NH_2$, methylamino, dimethylamino, ethylamino, diethylamino, propylamino, isopropylamino, phenylamino, or benzylamino. The term "alkylamino" may be defined as $NR_7R_8$, wherein at least one of $R_7$ and $R_8$ may be alkyl and the other may be alkyl or hydrogen. The term "arylamino" may be defined as $NR_9R_{10}$, wherein at least one of $R_9$ and $R_{10}$ may be aryl and the other may be aryl or hydrogen.

The term "halogen" or "halo," as used herein, refers to bromine, chlorine, fluorine, or iodine. In some embodiments, the halogen may be fluorine. In other embodiments, the halogen may be chlorine or bromine.

The various aspects and embodiments disclosed herein are for purposes of illustration and are not intended to be limiting, with the true scope and spirit being indicated by the following claims.

The invention claimed is:

1. A method for treating a keratinized tissue condition in a subject in need of treatment thereof, comprising:
   conducting one or more treatment cycles on the keratinized tissue in the subject in need of treatment thereof, each treatment cycle comprising:
      contacting the keratinized tissue with an acid-activated gas-generating composition, the acid-activated gas-generating composition consisting of:
         a gas generating agent; and
         one or more of: water, aloe vera extract, panthenol, a sugar, a nonionic surfactant, a preservative, a water soluble alkali metal halide salt, a water soluble alkali earth metal salt, an ionic surfactant, a sugar, or sea trace elements;
      contacting the keratinized tissue with an acid composition, the acid composition consisting of:
         an acid; and
         one or more of: water, aloe vera extract, panthenol, a sugar, a nonionic surfactant, a preservative, a water soluble alkali metal halide salt, a water soluble alkali earth metal salt, an ionic surfactant, a sugar, or sea trace elements; and
      allowing the acid composition and the acid-activated gas-generating composition to react effective to generate a gas at the keratinized tissue,
   the one or more treatment cycles being effective to at least partly ameliorate the keratinized tissue condition in the subject, the keratinized tissue condition selected from the group consisting of: acneiform eruptions, autoinflammatory syndromes, chronic blistering, conditions of the skin appendages, dermatitis, drug or agent eruptions, infection-related, papulosquamous hyperkeratosis, palmoplantar keratodermas, pruritis, psoriasis, conditions resulting from physical factors, or ionizing radiation-induced conditions.

2. The method of claim 1, at least one treatment cycle comprising contacting the keratinized tissue with the acid-activated gas-generating composition before contacting the keratinized tissue with the acid composition.

3. The method of claim 2, at least one treatment cycle comprising contacting the keratinized tissue with the acid composition before contacting the keratinized tissue with the acid-activated gas-generating composition.

4. The method of claim 1, further comprising conducting two or more of the treatment cycles in succession on the keratinized tissue.

5. The method of claim 1, at least one treatment cycle comprising rinsing the keratinized tissue after allowing the acid composition and the acid-activated gas-generating composition to react effective to generate the gas at the keratinized tissue.

6. The method of claim 1, at least one treatment cycle comprising contacting the keratinized tissue with the acid composition after conducting the one or more treatment cycles on the keratinized tissue.

7. The method of claim 1, further comprising adjusting the keratinized tissue to between a pH of about 4.5 and a pH of about 6.5 after conducting the one or more treatment cycles on the keratinized tissue.

8. The method of claim 1, the gas generating agent selected from the group consisting of: an alkali metal carbonate, alkali earth metal carbonate, an alkali metal bicarbonate, an alkali earth metal bicarbonate, and carbonic acid.

9. The method of claim 1, the acid selected from the group consisting of: lactic acid, acetic acid, formic acid, citric acid, oxalic acid, phosphoric acid, succinic acid, uric acid, and an acidic ammonium salt.

10. The method of claim 1, wherein the gas generating agent is sodium hydrogen carbonate.

11. The method of claim 1, the acid composition comprising citric acid, sodium chloride, magnesium chloride, dextrose, and sea trace elements.

12. The method of claim 1, wherein contacting the keratinized tissue with the acid-activated gas-generating composition and the acid composition varys a pH value at the surface of the keratinized tissue to vary between an alkaline state and an acidic state.

13. The method of claim 1, the keratinized tissue comprising a plurality of cuticles, wherein contacting the keratinized tissue with the acid-activated gas-generating composition and the acid composition varys a pH value at the surface of the keratinized tissue effective to cause at least a portion of the plurality of cuticles to switch between an open state and a closed state.

14. The method of claim 1, the keratinized tissue comprising a plurality of keratinized epidermal skin cells, wherein contacting the keratinized tissue with the acid-activated gas-generating composition and the acid composition varys a pH at the keratinized tissue effective to cause at least a portion of the plurality of keratinized epidermal skin cells to be shed from the keratinized tissue.

15. The method of claim 1, further comprising: preparing the acid-activated gas-generating composition by contacting the gas-generating agent with one or more of: water or a slip composition, the slip composition comprising one or more of: water, aloe vera extract, panthenol, a sugar, a nonionic surfactant, a preservative, a water soluble alkali metal halide salt, a water soluble alkali earth metal salt, an ionic surfactant, or sea trace elements.

16. The method of claim 1, further comprising: preparing the acid composition by contacting the acid with one or more of: water or a slip composition, the slip composition comprising one or more of: water, aloe vera extract, panthenol, a sugar, a nonionic surfactant, a preservative, a water soluble alkali metal halide salt, a water soluble alkali earth metal salt, an ionic surfactant, or sea trace elements.

\* \* \* \* \*